United States Patent
Röder et al.

(10) Patent No.: US 9,254,120 B2
(45) Date of Patent: *Feb. 9, 2016

(54) METHOD FOR PREDICTING BREAST CANCER PATIENT RESPONSE TO COMBINATION THERAPY

(71) Applicant: Biodesix, Inc., Boulder, CO (US)

(72) Inventors: Joanna Röder, Steamboat Springs, CO (US); Julia Grigorieva, Steamboat Springs, CO (US); Heinrich Röder, Steamboat Springs, CO (US)

(73) Assignee: Biodesix, Inc., Boulder, CO (US)

( * ) Notice: Subject to any disclaimer, the term of this patent is extended or adjusted under 35 U.S.C. 154(b) by 188 days.

This patent is subject to a terminal disclaimer.

(21) Appl. No.: 13/741,634

(22) Filed: Jan. 15, 2013

(65) Prior Publication Data

US 2013/0131996 A1 May 23, 2013

Related U.S. Application Data

(62) Division of application No. 13/356,730, filed on Jan. 24, 2012, now Pat. No. 8,914,238.

(60) Provisional application No. 61/437,575, filed on Jan. 28, 2011.

(51) Int. Cl.
| | |
|---|---|
| G01N 31/00 | (2006.01) |
| A61B 10/00 | (2006.01) |
| G01N 33/574 | (2006.01) |
| G01N 33/68 | (2006.01) |
| G06F 19/24 | (2011.01) |
| H01J 49/00 | (2006.01) |

(52) U.S. Cl.
CPC ...... *A61B 10/0041* (2013.01); *G01N 33/57415* (2013.01); *G01N 33/6848* (2013.01); *G01N 33/6893* (2013.01); *G06F 19/24* (2013.01); *G01N 2333/485* (2013.01); *G01N 2333/71* (2013.01); *G01N 2800/52* (2013.01); *H01J 49/00* (2013.01)

(58) Field of Classification Search
None
See application file for complete search history.

(56) References Cited

U.S. PATENT DOCUMENTS

| | | | |
|---|---|---|---|
| 5,693,463 | A | 12/1997 | Edwards et al. |
| 7,217,533 | B2 | 5/2007 | Osborne et al. |
| 7,402,402 | B2 | 7/2008 | Osborne et al. |
| 7,504,211 | B2 | 3/2009 | Huang et al. |
| 7,504,214 | B2 | 3/2009 | Erlander et al. |
| 7,537,891 | B2 | 5/2009 | Huang et al. |
| 7,642,050 | B2 | 1/2010 | Nevalainen et al. |
| 7,736,905 | B2 | 6/2010 | Roder et al. |
| 7,858,389 | B2 | 12/2010 | Roder et al. |
| 7,858,390 | B2 | 12/2010 | Roder et al. |
| 7,867,775 | B2 | 1/2011 | Roder et al. |
| 7,879,620 | B2 | 2/2011 | Roder et al. |
| 7,906,342 | B2 | 3/2011 | Roder et al. |
| 8,024,282 | B2 | 9/2011 | Tsypin et al. |
| 8,097,469 | B2 | 1/2012 | Roder et al. |
| 2005/0048547 | A1 | 3/2005 | Zhao et al. |
| 2005/0164218 | A1 | 7/2005 | Agus et al. |
| 2005/0239083 | A1 | 10/2005 | Erlander et al. |
| 2006/0029574 | A1 | 2/2006 | Albitar et al. |
| 2006/0275844 | A1 | 12/2006 | Linke |
| 2008/0199891 | A1 | 8/2008 | Ring et al. |
| 2010/0068717 | A1 | 3/2010 | Badve et al. |
| 2010/0120039 | A1 | 5/2010 | Fuqua |
| 2010/0305868 | A1 | 12/2010 | Roder et al. |
| 2011/0208433 | A1 | 8/2011 | Grigorieva et al. |

FOREIGN PATENT DOCUMENTS

| | | |
|---|---|---|
| WO | 2005094357 | 10/2005 |
| WO | 2007001868 | 1/2007 |

OTHER PUBLICATIONS

Taguchi et al. (J Natl Cancer Inst 2007;99: 838-46).*
International Search Report and Written Opinion in PCT application PCT/US12/00044, dated May 10, 2012.
Frederick et al., "Epithelial to mesenchymal transition predicts gefitinib resistance in cell lines of head and neck squamous cell carcinoma and non-small cell lung carcinoma", Molecular Cancer Therapeutics, 6(6):1683-1691 (2007).
Goldhirsch et al., "Endocrine therapy of breast cancer", Ann. Oncol. 13 Suppl. 4, pp. 61-68 (2002).
Ma et al., "Predicting endocrine therapy responsiveness in breast cancer", Oncology, 23(2):133-42 (2009).
Johnston et al., "Lapatinib combined with letrozole versus letrozole and placebo as first-line therapy for postmenopausal hormone receptor-positive metastatic breast cancer", J. Clin. Oncol. 27(33):5538-46 (2009).

(Continued)

*Primary Examiner* — Pablo S Whaley
(74) *Attorney, Agent, or Firm* — McDonnell Boehnen Hulbert & Berghoff LLP (57) ABSTRACT

A mass-spectral method is disclosed for determining whether breast cancer patient is likely to benefit from a combination treatment in the form of administration of a targeted anti-cancer drug in addition to an endocrine therapy drug. The method obtains a mass spectrum from a blood-based sample from the patient. The spectrum is subject to one or more predefined pre-processing steps. Values of selected features in the spectrum at one or more predefined m/z ranges are obtained. The values are used in a classification algorithm using a training set comprising class-labeled spectra and a class label for the sample is obtained. If the class label is "Poor", the patient is identified as being likely to benefit from the combination treatment. In a variation, the "Poor" class label predicts whether the patient is unlikely to benefit from endocrine therapy drugs alone, regardless of the patient's HER2 status.

8 Claims, 8 Drawing Sheets

(56) References Cited

OTHER PUBLICATIONS

Chlebowski et al., "Optimizing aromatase inhibitor integration into initial treatment strategies in postmenopausal women with hormone-receptor-positive early breast cancer", Breast Cancer Res. Treat, 112 Supp. 1, pp. 25-34 (2008).

Dowsett et al., "Meta-analysis of breast cancer outcomes in adjuvant trials of aromatase inhibitors versus tamoxifen", J. Clin. Oncol., 28(3):509-18 (2010).

Cuzick et al., "The ATAC trial: the vanguard trial for use of aromatase inhibitors in early breast cancer", Expert Rev. Anticancer Ther., 7(8):1089-94 (2007).

Tobias et al, "An open randomised trial of second-line endocrine therapy in advanced breast cancer: comparison of the Aromatase inhibitors letrozole and anastrozole", Eur. J. Cancer, 40(12):1913 (2004).

Zhen et al., "Serum Proteomic Profiles Suggest Celecoxib-Modulated Targets and Response Predictors", Cancer Research, 64:2904-2909 (2004).

Sergua et al., "Up-front Use of Araomatase Inhibitors as Adjuvant Therapy for Breast Cancer: The Emperor has no Clothes", J. Clin. Oncol., 27(6) (2009).

Lynch et al., "Activating Mutations in the Epidermal Growth Factor Receptor Underlying Responsiveness of Non-Small-Cell Lung Cancer to Gefitnib", New England Journal of Medicine, 350(21):2129-2139 (2004).

Maciel et al., "Differential proteomic serum pattern of low molecular weight proteins expressed by adenocarcinoma lung cancer patients", Journal of Experimental Therapeutics and Oncology, 5:31-38 (2005).

Haury et al., "The Influence of Feature Selection Methods on Accuracy, Stability and Interpretability of Molecular Signatures", PloS One, 6(12):e28210 (2011).

Ein-Dor et al, "Outcome signature genes in breast cancer: is there a unique set?" Bioinformatics, 21(2):171-178 (2005).

Chung et al., "Detection of Tumor Epidermal Growth Factor Receptor Pathway Dependence by Serum Mass Spectrometry in Cancer Patients", Cancer Epidemiol Biomarkers, 19(2):OF1-OF8 and Suppl. (2010).

Erjala et al., "Signaling via ErbB2 and ErbB3 Associates with Resistance and Epidermal Growth Factor Receptor (EGRF) Amplification with Sensitivity to EGRF Inhibotor Gefitinb in Head and Neck Squamous Cell Carcinoma Cells", Clin. Cancer Research, 12(13):4103-4111 (2006).

Su et al, "Pretreatment Epidermal Growht Factor Receptor (EGFR) T790M Mutation Predicts Shorter EGFR Tyrosine Kinase Inhibitor Response Duration in Patients with Non-Small-Cell Lung Cancer", Journal of Clinical Oncology, published online ahead of print at www.jco.org on Jan. 3, 2012.

Taguchi et al., "Mass Spectrometry to Classify Non-Small-Cell Lung Cancer Patients for Clinical Outcome After Treatment with Epidermal Growth Factor Receptor Tyrosine Kinase Inhibitors: A Multicohort Cross-Institutional Study", Journal of the National Cancer Institute, 99(11):838-46 (2007).

Johnston, "Enhancing the Efficacy of Hormonal Agents with Selected Targeted Agents", Clinical Breast Cancer, vol. 9, Suppl. 1, S28-S36, 2009.

\* cited by examiner

Fig. 3
Letrozole Arm

Fig. 4
VeriStrat Good Patients

Fig. 5
VeriStrat Poor Patients

Fig. 6

Fig. 9
HER2- VeriStrat Good Patients

Fig. 10
HER2- VeriStrat Poor Patients

Fig. 11

Fig. 12
HER2+ VeriStrat Good Patients

Fig. 13
HER2+ VeriStrat Poor Patients

METHOD FOR PREDICTING BREAST CANCER PATIENT RESPONSE TO COMBINATION THERAPY

CROSS-REFERENCE TO RELATED APPLICATIONS

This application is a divisional application of U.S. Ser. No. 13/356,730, filed Jan. 24, 2012, which claims priority benefits under 35 U.S.C. §119(e) to U.S. Provisional application Ser. No. 61/437,575 filed Jan. 28, 2011, the contents of which are incorporated by reference herein.

BACKGROUND

This application relates generally to the field of treatment of breast cancer and more particularly to a predictive test for determining, in advance of treatment, whether a breast cancer patient is a member of a class of patients that would be likely to benefit from a combination of certain anti-cancer drugs. The application also relates to a predictive test for determining, in advance of treatment, whether a breast cancer patient is a member of a class of patients that would not be likely to benefit from endocrine therapy alone, including for example an aromatase inhibitor such as letrozole.

The applicant's Assignee Biodesix, Inc. has developed a predictive test for determining whether certain cancer patients would be likely to benefit from anti-cancer drugs or combinations of drugs. The commercial version of the test, known as VERISTRAT®, is a MALDI-ToF mass spectrometry serum-based test that has clinical utility in the selection of specific targeted therapies in solid epithelial tumors. See U.S. Pat. No. 7,736,905, the content of which is incorporated by reference herein, which describes the test in detail. In brief, a mass spectrum of a serum sample of a patient is obtained. After certain pre-processing steps are performed on the spectrum, the spectrum is compared with a training set of class-labeled spectra of other cancer patients with the aid of a classifier. The class-labeled spectra are associated with two classes of patients: those that benefitted from epidermal growth factor receptor inhibitors (EGFRIs), class label of "Good", and those that did not, class label of "Poor". The classifier assigns a class label to the spectrum under test. The class label for the sample under test is either "Good" or "Poor," or in rare cases where the classification test fails the class label for the sample is deemed "undefined."

Patients whose sample is identified by the test as Poor are identified as members of a group or class of patients which appear to be unlikely to obtain clinical benefit from treatment with epidermal growth factor receptor inhibitors (EGFRIs) such as gefitinib (Iressa®), erlotinib (Tarceva®), and cetuximab (Erbitux®) in the treatment of solid epithelial tumors. The complementary patient population, associated with the class label of Good, is likely to benefit depending on the details of the indication. In the absence of treatment, the VeriStrat test has a strong prognostic component, meaning that "Poor" patients perform significantly worse than "Good" patients.

The VeriStrat Poor signature has been found in a variety of solid tumors including non-small cell lung cancer (NSCLC), colorectal cancer (CRC), and squamous cell cancer of the head and neck (SCCHN or, alternatively, H&N). The following patents documents of the applicant's assignee describe further background information concerning the VeriStrat test and its applications: U.S. Pat. Nos. 8,024,282; 7,906,342; 7,879,620; 7,867,775; 7,858,390; 7,858,389 and 7,736,905.

Breast cancer is the leading form of cancer in women and the second leading cause of cancer death in women, after lung cancer. The development of breast cancer is believed to be a multi-step process of genetic alteration that transforms normal cells into highly malignant derivatives.

It has been known for many years that changing the hormonal balance of a patient with breast cancer could lead to changes in tumor growth and regression of metastatic disease. Estrogen in particular can promote the growth of breast cancer cells. Accordingly, while treatment of breast cancer can follow several avenues, including surgery and chemotherapy, so-called endocrine therapies that are designed to block the generation or uptake of estrogen are commonly used in treatment of breast cancer. See generally A. Goldhirsch et al. [1]. Currently, one of the most promising avenues of endocrine therapy takes the form of administration of drugs that modulate estrogen synthesis and inhibit estrogen receptor pathways.

Agents targeting estrogen receptors include selective estrogen receptor modulators (SERMs) and selective estrogen receptor downregulators (SERDs). Both SERDs and SERMs are in use in treatment of breast cancer. Tamoxifen, a most often used agent in pre-menopausal setting, is an estrogen receptor antagonist in breast tissue, but acts as an agonist in some other tissues, hence it belongs to the SERM class. In post-menopausal women tamoxifen is also used, as well as some other antagonists, such as Fulvestrant (a SERD) and toremifine (a SERM). Tamoxifen, a non-steroidal antiestrogen, is thought to inhibit breast cancer growth by competitively blocking estrogen receptor (ER), thereby inhibiting estrogen-induced growth. ER is a ligand-dependent transcription factor activated by estrogen. Upon interaction with the hormone it enters the nucleus, binds to specific DNA sequences and activates ER-regulated genes, mediating most biological effects of estrogens on normal cells and estrogen-dependent tumors.

Endocrine therapy drugs also include a class of drugs known as aromatase inhibitors, including selective and non-selective aromatase inhibitors. Selective aromatase inhibitors include letrozole, as well as anastrozole (arimidex); another similar acting, however non-reversible, agent is exemestane (aromasin). Aromatase is an enzyme that synthesizes estrogen in the body by converting the hormone androgen into estrogen. Aromatase inhibitors stop the production of estrogen by blocking the aromatase. Administration of aromatase inhibitors thus reduces the amount of estrogen which is available to stimulate the growth of hormone receptor-positive breast cancer cells. In post-menopausal settings letrozole, anastrozole, and exemestane are aromatase inhibitors (AIs) that are used most frequently.

Many breast cancer patients have a primary resistance or develop tumor resistance to endocrine therapy despite detected hormone receptor (HR)-positive status. The art has recognized a variety of methods for attempting to predict resistance to endocrine therapy in breast cancer patients. See U.S. Pat. Nos. 7,217,533; 7,642,050; 7,504, 214; 7,402,402; 7,537,891, 7,504,211; 5,693,463 and the article of Ma et al [2]. These methods typically involve either determining whether breast cancer cells express certain gene expression products or profiles, or analyzing certain ratios of certain gene expression products.

SUMMARY

Up to 50% of women with breast cancers that are hormone receptor-positive do not derive benefit from endocrine therapy modulating tumor estrogen receptor function or reducing the level of circulation estrogens. [2]

We have discovered a method for determining whether a hormone receptor positive breast cancer patient, regardless of their HER2 status, is unlikely to benefit from administration of an endocrine therapy drug alone for treatment of the cancer. Unlike the prior art, our methods involve a mass-spectrometry test that uses a blood-based sample from the patient (serum or plasma) to make this determination. This method involves a) obtaining a mass spectrum from a blood-based sample from the patient; b) performing one or more predefined pre-processing steps on the mass spectrum obtained in step a); c) obtaining values of selected features in the mass spectrum at one or more predefined m/z ranges after the pre-processing steps on the mass spectrum in step b) have been performed; and d) using the values obtained in step c) in a classification algorithm using a training set comprising class-labeled spectra produced from samples from other cancer patients and obtaining a class label for the sample. The class label assigned to the mass spectrum by the classification algorithm predicts whether the breast cancer patient is likely to benefit. In particular, if the class label obtained in step d) is "Poor" or the equivalent, the patient is identified as being unlikely to benefit from the endocrine therapy drug.

In another aspect, we have discovered a mass-spectrometry test or method of determining whether a post-menopausal hormone receptor positive breast cancer patient with HER2 negative status is likely to benefit from administration of a combination treatment comprising administration of a targeted anti-cancer drug in addition to an endocrine therapy drug. Our method includes the steps of a) obtaining a mass spectrum from a blood-based sample from the patient; b) performing one or more predefined pre-processing steps on the mass spectrum obtained in step a); c) obtaining values of selected features in said spectrum at one or more predefined m/z ranges after the pre-processing steps on the mass spectrum in step b) have been performed; and d) using the values obtained in step c) in a classification algorithm using a training set comprising class-labeled spectra produced from samples from other cancer patients and obtaining a class label for the sample. If the class label obtained in step d) is "Poor" or the equivalent then the patient is identified as being likely to benefit from the combination treatment.

We have arrived at these methods by examining the effect of separation of blood-based samples using the VeriStrat test on the treatment efficacy of letrozole with or without lapatinib in first line metastatic breast cancer patients in a retrospective analysis of the phase III trial EGF30008 [3]. The total number of patients in this trial was 1258, 1164 pretreatment serum samples were available for analysis. We obtained valid VeriStrat test results for 1046 of these patients, of which 961 were classified as VeriStrat Good, 80 were VeriStrat Poor, and 5 were VeriStrat Indeterminate (Undefined) (patients for whom 3 replicate spectra produced discrepant results); 117 samples were not evaluable due to hemolysis and we could not assign a VeriStrat label to one patient due to data inconsistencies between available samples.

As a result of the analysis of EGF30008 we have made several observations leading to the present inventive methods. One of which is that, for those patients having a mass spectral signature that is classified as "poor" using the training set, that class label identifies those patients that are not likely to benefit from administration of endocrine therapy alone, regardless of their HER2 status. Such patients can be characterized as "endocrine resistant", i.e., resistant to endocrine therapy drugs. Patients with hormone-receptor positive status are considered to be sensitive to endocrine therapy, however up to 40-50% of them do not respond to it from the beginning of treatment or stop responding at some point in the course of treatment. That's why our finding that we can identify a subset not benefiting from endocrine therapy (despite being hormone receptor-positive) is an important result. Since the patient is predicted to not benefit in advance of treatment, the patient can be steered into the direction of other treatments that are more likely to lead to a favorable outcome from the start.

In pre-menopausal women estrogen is produced mainly in the ovaries, hence, the treatment strategy for the HR-positive breast cancer in this population involves ovarian suppression usually in combination with ER modulator, tamoxifen. In post-menopausal women ovarian function has ceased and estrogen is synthesized in smaller quantities from androgens. Aromatase plays a key role in this process, providing a biological rationale for using aromatase inhibitors (AIs) for treatment of HR-positive breast cancer in post-menopausal women. Both ER modulators (tamoxifen) and aromatase inhibitors show effectiveness in post-menopausal women. Recent publications provide conflicting advice on the role of AIs in the treatment of postmenopausal patients with early-stage hormone receptor-positive breast cancer. On one hand, Chlebowski [4] recommends up-front AI for the majority of patients, whereas Seruga and Tannock [5] suggest that tamoxifen remains the endocrine treatment of choice for most patients. Meta-analysis of breast cancer outcomes in adjuvant trials of aromatase inhibitors versus tamoxifen in post-menopausal women showed that AIs produce significantly lower recurrence rates compared with tamoxifen, either as initial monotherapy or after 2 to 3 years of tamoxifen. At 5 years, AI therapy was associated with an absolute 2.9% decrease in recurrence and a nonsignificant absolute 1.1% decrease in breast cancer mortality [6]. The ATAC trial of Anastrozole, Tamoxifen, Alone or in Combination showed that 5 years of treatment with anastrozole was generally better tolerated than 5 years of treatment with tamoxifen, and led to lower recurrence rates, especially in hormone receptor-positive women (26% reduction), however the benefits on late end points, such as distant recurrence and death after recurrence, were marginal [7]. Comparisons of various AIs in randomized clinical trials show that while there is some difference in the outcomes, it is often difficult to choose between the agents. For example in a comparative trial of aromatase inhibitors letrozole and anastrozole, letrozole was significantly superior to anastrozole in the overall response rate (ORR), however there were no significant differences between the treatment arms in the rate of clinical benefit, median duration of response, duration of clinical benefit, time to treatment failure, or overall survival. [8] Similarity of the mechanisms of action as well as of clinical outcomes in clinical trials with different AIs give us a reason to expect that separation of breast cancer patients by VeriStrat test with respect to clinical benefit observed with letrozole is likely to be similar to other AIs. In addition, taking into consideration that both tamoxifen's and AIs' therapeutic effects are based on the reduction of activated hormone—ER receptor complexes in the cell, either through the inhibition of estrogen synthesis or minimization of number of receptors available for ligand binding, one can hypothesize that the effect observed in the study with one of AIs (letrozole) is likely to be similar in the case of treatment with an estrogen modulator tamoxifen. Hence, the VeriStrat test may be of significant clinical utility in various types of hormonal therapy of breast cancer.

Furthermore, we have observed that the addition of lapatinib to letrozole significantly improves patient outcome in the "Poor" group but has little or no clinical benefit in the "Good" group. This observation holds even under further stratification into HER2positive (HER2+) and HER2-negative (HER2-)strata. Our mass-spectrometry test was shown to be a predictive test for the benefit of adding lapatinib to letrozole treatment as the p-value of treatment*VeriStrat status interaction was found to be significant, and this significance remained even in multivariate analysis adjusted for possible confounding factors. While it is not surprising that there is benefit from adding lapatinib to letrozole in HER2+ patients, the observation that adding lapatinib to letrozole in HER2- patients can lead to a substantial improvement in progression free survival in a selected population is unexpected. This patient subgroup can be identified by a mass-spectrometry test conducted on a blood-based sample in advance of treatment. This patient selection process may lead to improved treatment paradigms. For example, one could test all hormone receptor positive patients for VeriStrat status (i.e., class label "Good" or "Poor"); if a patient were classified as Poor they would be likely to benefit from the addition of lapatinib to letrozole irrespective of the patient's HER2 status. If a patient's VeriStrat status were VeriStrat Good, one could then perform a HER2 test to decide whether the addition of lapatinib would be appropriate. Alternatively, if the HER2 status were known to be HER2-negative, one can perform the VeriStrat test to decide whether the patient belongs to the VeriStrat Poor subgroup and may benefit from the addition of lapatinib.

Given the result obtained with the dual HER2/EGFR inhibitor lapatinib, one can expect similar effects in VeriStrat Poor patients with HER2-negative status from the addition to letrozole of other agents targeting HER2/EGFR, e.g. neratinib, afatinib, or combinations of agents aimed at the same receptors, e.g. erlotinib or gefitinib plus trastuzumab.

BRIEF DESCRIPTION OF THE DRAWINGS

FIGS. 2-13 show data resulting from our retrospective analysis of the phase III EGF 30008 trial, and in particular:

FIG. 2 shows that patients have similar outcomes on the combination of lapatinib and letrozole regardless of their VeriStrat status, but not on letrozole alone. In particular, FIG. 2 shows that, for those patients treated with letrozole alone, patients identified as "Poor" do much worse on letrozole alone than those patients identified as "Good. " FIG. 2 also shows that patients whose serum was classified as "Poor" showed improved progression free survival (PFS) with the addition of lapatinib to letrozole.

FIG. 3 demonstrates that our VeriStrat test identifies a group of patients with poor outcomes on letrozole alone.

FIG. 5 illustrates that patients whose serum is classified as "Poor" benefit significantly more with combination treatment (lapatinib and letrozole) than those receiving letrozole alone; the median PFS is greater by 8.2 months with combination treatment. The significance of the difference in benefit is demonstrated in the multivariate analysis with the interaction term included.

FIGS. 7 and 8 show that our test identifies patients with poor outcomes on letrozole alone, independent of HER2 status.

FIG. 10 demonstrates that HER2- patients whose serum is classified as "Poor" showed a trend for improved PFS with the addition of lapatinib to letrozole as compared to treatment by letrozole alone.

FIGS. 11-13 demonstrate that, within the population of HER2+ patients, patients have similar outcomes with lapatinib plus letrozole regardless of their VeriStrat classification.

DETAILED DESCRIPTION

Our work leading to the present inventive methods involved evaluating the effect of VeriStrat separation ("Good" vs. "Poor") on the treatment efficacy of letrozole with or without lapatinib in first line metastatic breast cancer patients in a retrospective analysis of the phase III trial EGF30008 (see S Johnston et al, [3] attached as an appendix to our prior provisional application). Our work involved obtaining serum samples from patients involved in this study, obtaining mass spectra of such samples, and subjecting the spectra to a classifier we have developed and described in our U.S. Pat. No. 7,736,905. The classifier assigned a class label to the samples, either "Good" or "Poor" or in a few instances "undefined." The class labels were assigned using a K-nearest neighbor (KNN) scoring algorithm based on a comparison of the spectra, after preprocessing and calculation of integrated intensity values at selected features in the spectra, with a training set of class-labeled spectra from other cancer patients.

In the study we conducted, the training set used by the classification algorithm used class-labeled spectra from a population of non-small cell lung cancer patients, with the class-label in the training set being "Good" if the associated spectra in the training set was assigned to a patient who benefitted from administration of an EGFR-I, whereas the class label "Poor" was assigned to spectra for patients who did not benefit from such drugs. This training set and the classifier was the subject of extensive validation studies. The method of conducting our mass-spectral testing and classification of blood-based samples is explained in further detail below.

In our retrospective analysis of the EGF30008 study, we obtained serum samples from the patients participating in the study, subjected them to our VeriStrat test, and the samples were assigned class labels of Good or Poor, depending on the outcome of the KNN algorithm in the classifier. We studied these class labels, along with clinical data associated with the patients in this study and made a number of surprising discoveries.

In particular, as a result of the analysis of EGF30008, and our understanding of the drugs involved in this study, we have discovered that our mass spectral testing method provides the ability to identify a certain class of hormone receptor positive breast cancer patients that are not likely to benefit from endocrine therapy drugs alone in treatment of the cancer. This class of patient is identified when the classifier assigns the "Poor" class label to the sample's mass spectrum.

We also discovered that the addition of lapatinib to letrozole significantly improves patient outcome in the "Poor" group but has little or no clinical benefit for those patients identified as "Good". This observation holds even under further stratification into HER2+ and HER2− strata. Our mass-spectral test was shown to be a predictive test for the benefit of adding lapatinib to letrozole treatment as the p-value of treatment*VeriStrat status interaction was found to be significant, and this significance remained even in multivariate analysis adjusted for possible confounding factors.

While it is not surprising that there is benefit from adding lapatinib to letrozole in HER2+ patients, the observation that adding lapatinib to letrozole in HER2− patients can lead to a substantial improvement in progression free survival in a selected population is unexpected. This patient subgroup can be identified by mass-spectrometry testing on a serum sample in advance of treatment, and this patient selection may lead to improved treatment paradigms. For example, one could test all hormone receptor positive patients for VeriStrat status; if a patient were classified as Poor they would benefit from the addition of lapatinib to letrozole irrespective of the patient's HER2 status. If a patient's VeriStrat status were Good, then one could perform a HER2 test to decide whether the addition of lapatinib would be appropriate. Alternatively, if HER2 status is known, one can perform the VeriStrat test on HER2-negative patients and identify those (VeriStrat Poor) patients who would benefit from the addition of lapatinib The discoveries resulting from our study of these samples and the VeriStrat testing can take the form of practical, useful tests. One aspect is that our testing method identifies a group of hormone receptor positive breast cancer patients that are not likely to benefit from administration of an endocrine therapy drug alone. This identification can be made in advance of treatment.

In this first aspect, the method is described herein for determining whether a hormone receptor positive breast cancer patient, regardless of the patients' HER2 status, is unlikely to benefit from administration of an endocrine therapy drug alone for treatment of the cancer. The method includes the steps of: a) obtaining a mass spectrum from a blood-based sample from the patient; b) performing one or more predefined pre-processing steps on the mass spectrum obtained in step a); c) obtaining values of selected features in the spectrum at one or more predefined m/z ranges after the pre-processing steps on the mass spectrum in step b) have been performed; d) using the values obtained in step c) in a classification algorithm using a training set comprising class-labeled spectra produced from samples from other cancer patients and obtaining a class label for the patient's sample; and e) if the class label obtained in step d) is "Poor" or the equivalent, then the patient is identified as being unlikely to benefit from the treatment.

Those patients that do not respond well to endocrine therapy drugs alone can be said to be "endocrine resistant." That is, patients with hormone-receptor positive status are considered to be sensitive to endocrine therapy, however some of them do not respond to it from the beginning of treatment, while others can stop responding at some point. Our finding that we can identify the subset of patients that is predicted to not benefit from endocrine therapy drugs (despite being hormone receptor-positive), and that identification can be made in advance of initiating treatment, is an important result.

A second practical test is described herein in the form of a method of determining whether a post-menopausal hormone receptor positive breast cancer patient with HER2-negative status is likely to benefit from administration of a combination treatment comprising administration of a targeted anti-cancer drug in addition to an endocrine therapy drug. The method involves the steps of: a) obtaining a mass spectrum from a blood-based sample from the patient; b) performing one or more predefined pre-processing steps on the mass spectrum obtained in step a); c) obtaining values of selected features in said spectrum at one or more predefined m/z ranges after the pre-processing steps on the mass spectrum in step b) have been performed; d) using the values obtained in step c) in a classification algorithm using a training set comprising class-labeled spectra produced from samples from other cancer patients and obtaining a class label for the sample; and e) if the class label obtained in step d) is "Poor" or the equivalent then the patient is identified as being likely to benefit from the combination treatment.

Cross-talk between pathways involved with estrogen receptors and HER2 and EGFR is considered as one of the primary mechanisms of this resistance to letrozole alone and constitutes the rationale for the combination of drugs (targeted therapies and endocrine therapies) used in our study, since inhibition of production of estrogen and at the same time of HER2 and EGFR signaling, stops these interactions and helps to prevent/overcome resistance. Here, the important finding we have made is that patients that seemed to be resistant (non-benefiting) to letrozole alone respond to the combination of targeted therapies and endocrine therapies (e.g., the combination of lapatinib plus aromatase inhibitor such as letrozole), and, most interestingly, in the HER2-negative group as well if they are classified as "Poor" in our test. HER2-negative patients were not expected to gain benefit from the combination treatment, but we have been able to identify a subgroup of HER2-negative patients that are likely to benefit from the combination treatment, which is a significant advance.

The VeriStrat Test

The methods of this disclosure for identifying a set of hormone receptor positive breast cancer patients that are not likely to benefit from an endocrine therapy (e.g., aromatase inhibitor, tamoxifen, other SERMs and SERDs) alone, or alternatively to benefit from the addition of certain targeted therapies and endocrine therapy drugs, involves obtaining a blood-based sample (serum or plasma) of the breast cancer patient and processing it in accordance with the test described in this section of this document. The class label assigned to the specimen indicates whether the patient is unlikely to benefit from the administration of the endocrine therapy drug alone, or alternatively likely to benefit from the administration of a combination of a targeted therapy and an endocrine therapy drug. The test is illustrated in flow chart form in FIG. 1 as a process 100.

Figure 1:
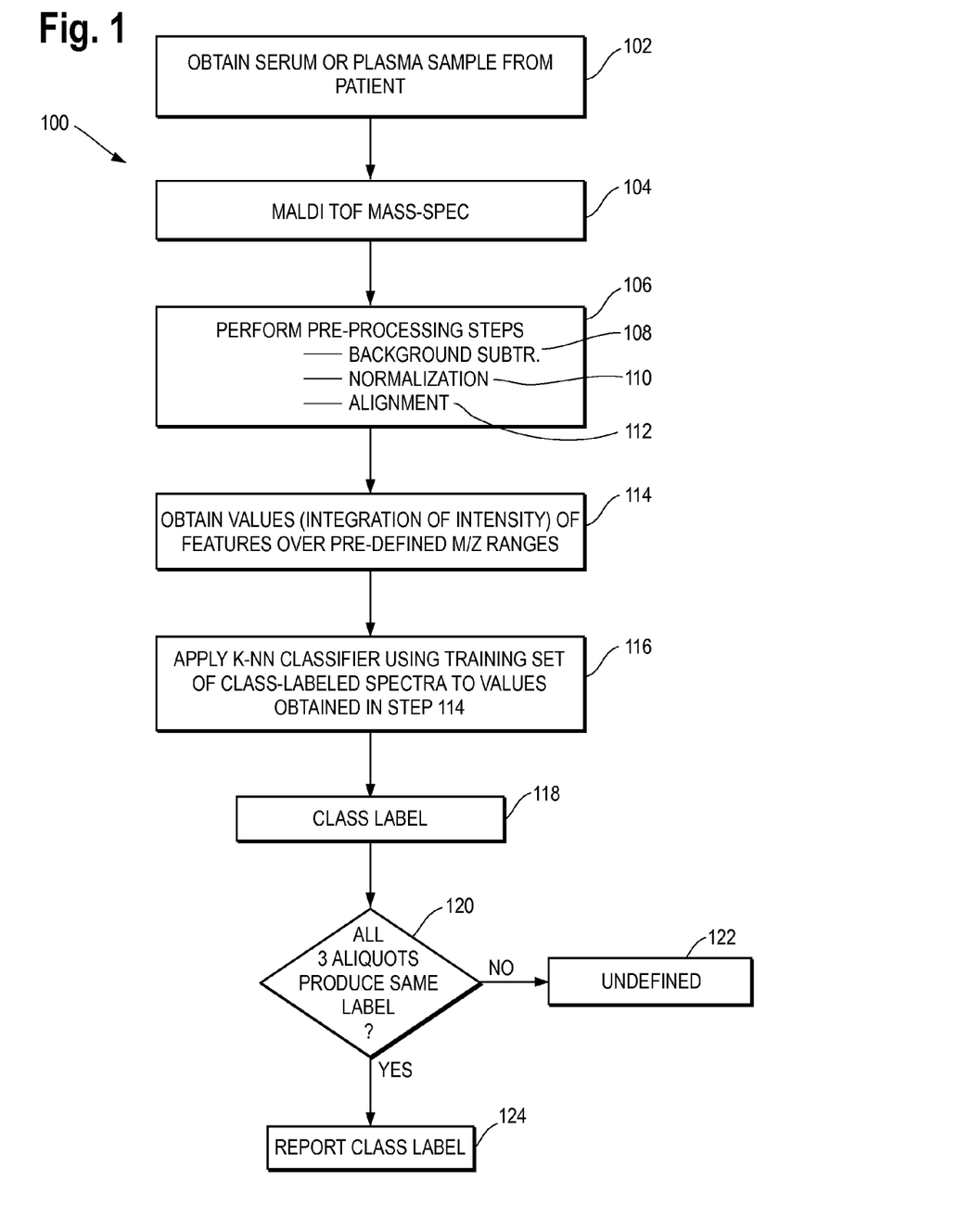
FIG. 1 is a block diagram showing a mass-spectrometry based test for predicting breast cancer patient response to certain drugs or combination of drugs for use in the methods of this disclosure.

At step 102, a serum or plasma sample is obtained from the patient. In one embodiment, the serum samples are separated into three aliquots and the mass spectroscopy and subsequent steps 104, 106 (including sub-steps 108, 110 and 112), 114, 116 and 118 are performed independently on each of the aliquots. The number of aliquots can vary, for example there may be 4, 5 or 10 aliquots, and each aliquot is subject to the subsequent processing steps.

At step 104, the sample (aliquot) is subject to mass spectroscopy. A preferred method of mass spectroscopy is matrix assisted laser desorption ionization (MALDI) time of flight (TOF) mass spectroscopy, but other methods are possible. Mass spectroscopy produces data points that represent intensity values at a multitude of mass/charge (m/z) values, as is conventional in the art. In one example embodiment, the samples are thawed and centrifuged at 1500 rpm for five minutes at four degrees Celsius. Further, the serum samples may be diluted 1:10, or 1:5, in MilliQ water. Diluted samples may be spotted in randomly allocated positions on a MALDI plate in triplicate (i.e., on three different MALDI targets). After 0.75 ul of diluted serum is spotted on a MALDI plate, 0.75 ul of 35 mg/ml sinapinic acid (in 50% acetonitrile and 0.1% trifluoroacetic acid (TFA)) may be added and mixed by pipetting up and down five times. Plates may be allowed to dry at room temperature. It should be understood that other techniques and procedures may be utilized for preparing and processing serum in accordance with the principles of the present invention.

Mass spectra may be acquired for positive ions in linear mode using a Voyager DE-PRO or DE-STR MALDI TOF mass spectrometer with automated or manual collection of the spectra. Seventy five or one hundred spectra are collected from seven or five positions within each MALDI spot in order to generate an average of 525 or 500 spectra for each serum specimen. Spectra are externally calibrated using a mixture of protein standards (Insulin (bovine), thioredoxin (*E. coli*), and Apomyglobin (equine)).

At step 106, the spectra obtained in step 104 are subject to one or more pre-defined pre-processing steps. The pre-processing steps 106 are implemented in a general purpose computer using software instructions that operate on the mass spectral data obtained in step 104. The pre-processing steps 106 include background subtraction (step 108), normalization (step 110) and alignment (step 112). The step of background subtraction preferably involves generating a robust, asymmetrical estimate of background in the spectrum and subtracts the background from the spectrum. Step 108 uses the background subtraction techniques described in U.S. Pat. No. 7,736,905, which is incorporated by reference herein. The normalization step 110 involves a normalization of the background subtracted spectrum. The normalization can take the form of a partial ion current normalization, or a total ion current normalization, as described in U.S. Pat. No. 7,736,905. Step 112 aligns the normalized, background subtracted spectrum to a predefined mass scale, as described in U.S. Pat. No. 7,736,905, which can be obtained from investigation of the training set used by the classifier.

Once the pre-processing steps 106 are performed, the process 100 proceeds to step 114 of obtaining values of selected features (peaks) in the spectrum over predefined m/z ranges. Using the peak-width settings of a peak finding algorithm, the normalized and background subtracted amplitudes may be integrated over these m/z ranges and assigned this integrated value (i.e., the area under the curve between the width of the feature) to a feature. For spectra where no peak has been detected within this m/z range, the integration range may be defined as the interval around the average m/z position of this feature with a width corresponding to the peak width at the current m/z position. This step is also disclosed in further detail in U.S. Pat. No. 7,736,905.

At step 114, as described in U.S. Pat. No. 7,736,905, the integrated values of features in the spectrum is obtained at one or more of the following m/z ranges:
5732 to 5795
5811 to 5875
6398 to 6469
11376 to 11515
11459 to 11599
11614 to 11756
11687 to 11831
11830 to 11976
12375 to 12529
23183 to 23525
23279 to 23622 and
65902 to 67502.

In a preferred embodiment, values are obtained at eight of these m/z ranges shown in Table 1 below. The significance, and methods of discovery of these peaks, is explained in the U.S. Pat. No. 7,736,905.

At step 116, the values obtained at step 114 are supplied to a classifier, which in the illustrated embodiment is a K-nearest neighbor (KNN) classifier. The classifier makes use of a training set of class labeled spectra from a multitude of other patients (which may be NSCLC cancer patients, or other solid epithelial cancer patients, e.g., HNSCC, Breast Cancer). The application of the KNN classification algorithm to the values at 114 and the training set is explained in U.S. Pat. No. 7,736,905. Other classifiers can be used, including a probabilistic KNN classifier or other classifier. In the illustrated embodiment, the training set is in the form of class-labeled spectra from NSCLC patients that either did or did not benefit from administration of EGFR inhibitors, those that did benefit being labeled "Good" and those that did not labeled "Poor."

Note that, in the illustrated embodiments of our predictive tests for breast cancer patient treatment, the classifier uses a training set from patients that are not breast cancer patients, but the predictions made by the method are nevertheless valid. The reason for using the NSCLC training set for the present study is that it has been subject to extensive validation. However, it is certainly possible to construct a training set and to validate it from test spectra obtained from a multitude of breast cancer patients. For example, the set of spectra we used in the EGF30008 study could be used to construct the training set and used in the classification of the test sample. Such an endeavor would have required substantial additional validation work which was not necessary in our case since the NSCLC training set used in the classifier performed so well.

At step 118, the classifier produces a label for the spectrum, either "Good", "Poor" or "Undefined". As mentioned above, steps 104-118 are performed in parallel on the three separate aliquots from a given patient sample (or whatever number of aliquots are used). At step 120, a check is made to determine whether all the aliquots produce the same class label. If not, an undefined (or Indeterminate) result is returned as indicated at step 122. If all aliquots produce the same label, the label is reported as indicated at step 124.

As described in this document, new and unexpected uses of the class label reported at step 124 are disclosed. For example, those hormone receptor positive, HER2-negative breast cancer patients labeled "Poor" in accordance with the VeriStrat test are likely to benefit from treatment in the form of an endocrine therapy drug, e.g., an aromatase inhibitor (letrozole) in combination with targeted therapy (e.g., lapatinib) in accordance with the present disclosure. As another example, regardless of the HER2 status, if the patient is identified as "Poor" in accordance with the test, then the patient is not likely to benefit from administration of an endocrine therapy drug alone.

It will be understood that steps 106, 114, 116 and 118 are typically performed in a programmed general purpose computer using software coding the pre-processing step 106, the obtaining of spectral values in step 114, the application of the KNN classification algorithm in step 116 and the generation of the class label in step 118. The training set of class labeled spectra used in step 116 is stored in memory in the computer or in a memory accessible to the computer.

The method and programmed computer may be advantageously implemented at a laboratory test processing center as described in our prior patent application publication U.S. Pat. No. 7,736,905.

TABLE 1

| Peaks used in VeriStrat. | |
|---|---|
| Peak number | m/z |
| 1 | 5843 |
| 2 | 11445 |
| 3 | 11529 |
| 4 | 11685 |
| 5 | 11759 |
| 6 | 11903 |
| 7 | 12452 |
| 8 | 12579 |

Discussion and Supporting Data

Our results from this retrospective analysis of the EGF30008 study are shown in FIGS. 2-13 and the data supporting our conclusions will be discussed below.

Figure 3:
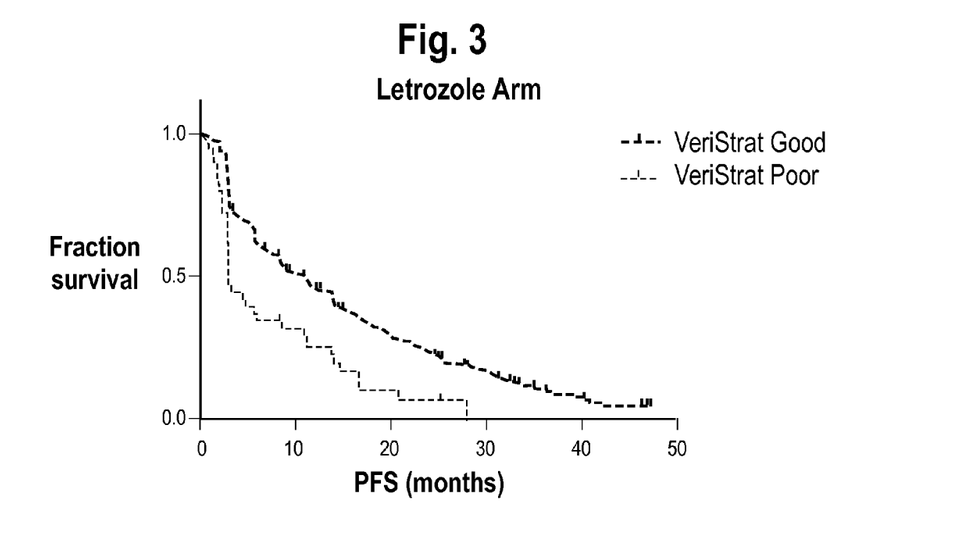
FIG. 3 is a Kaplan-Meier plot of PFS for the letrozole arm by VeriStrat classification.

FIG. 3 is a Kaplan-Meier plot of PFS for the letrozole+placebo arm of the EGF30008 study by VeriStrat classification. FIG. 3 demonstrates that our VeriStrat test identifies a group of patients with poor outcomes on letrozole alone. In particular, in the letrozole+placebo arm, there was significant separation between VeriStrat Good and VeriStrat Poor patients, with hazard ratio (HR)=0.36 (95% Confidence Interval (CI): 0.23-0.58) and log-rank p<0.0001. The median PFS was 10.8 months for VeriStrat Good patients (n=479) and 2.8 months for VeriStrat Poor patients (n=43).

The letrozole+lapatinib arm (not shown) showed no statistically significant separation between VeriStrat Good and VeriStrat Poor patients (log-rank p=0.53). Median PFS was 11.4 months for Good patients and 11.0 months for Poor patients.

Figure 4:
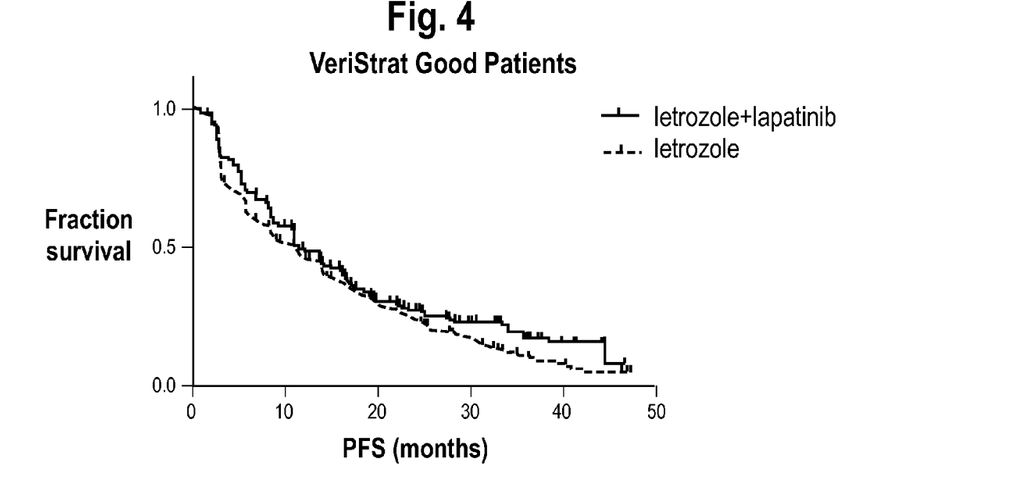
FIG. 4 is a Kaplan-Meier plot of PFS for "Good" patients by treatment arm.
Figure 5:
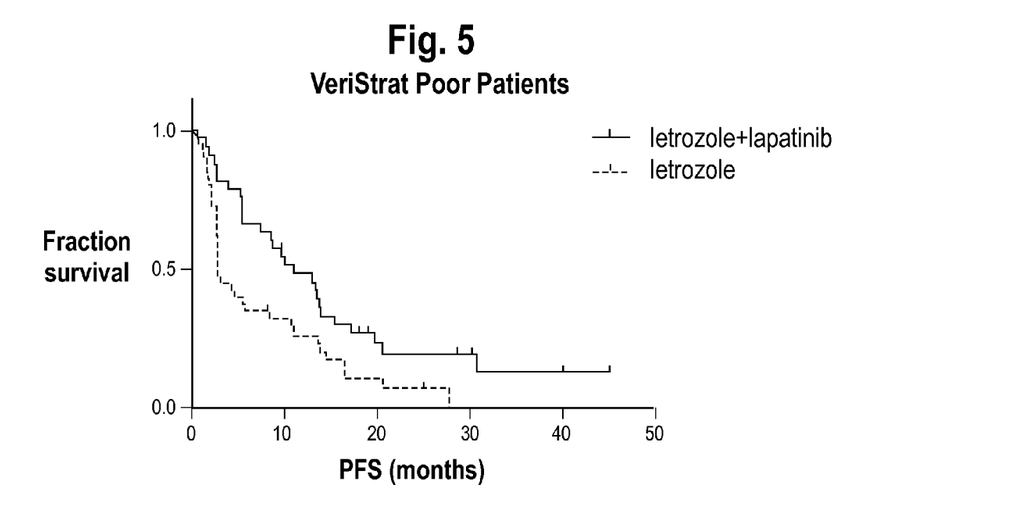
FIG. 5 is a Kaplan-Meier plot of PFS for "Poor" patients by treatment arm.
Figure 6:
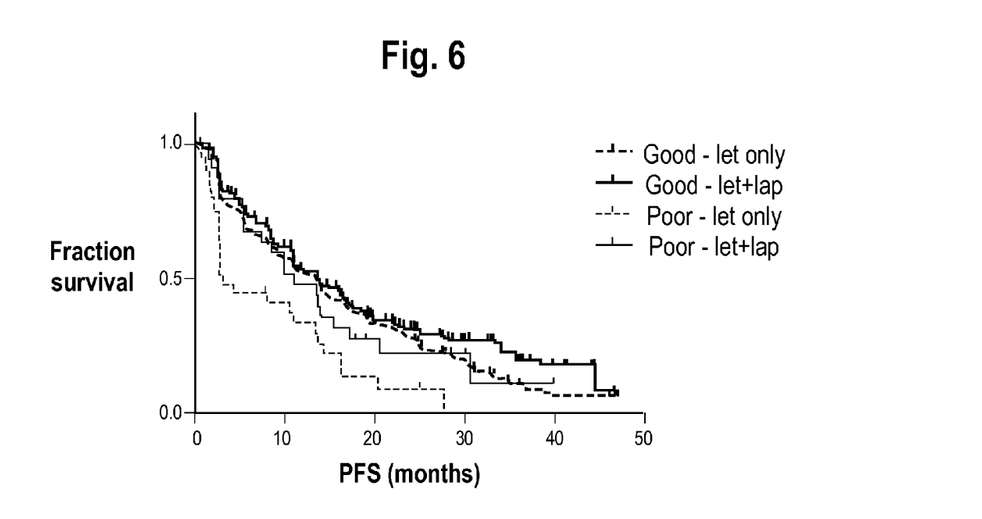
FIG. 6 is a Kaplan-Meier plot of PFS for by VeriStrat classification and treatment arm for HER2- population.

The effect on PFS with the addition of a targeted therapy (lapatinib) in addition to letrozole, separated by VeriStrat classification, is shown in FIGS. 4, 5 and 6. VeriStrat "Good" patients are shown in FIG. 4 and "Poor" patients in FIG. 5. There was significant separation in both VeriStrat classification groups in favor of letrozole+lapatinib treatment, but the separation was much larger for "Poor" patients. For "Good" patients (FIG. 4), the HR between treatment arms was HR=0.84 (95% CI: 0.72-0.98) and log-rank p=0.028. The median PFS was 11.4 months for the combination arm and 10.8 months for the letrozole+placebo arm.

For VeriStrat "Poor" patients (FIG. 5), HR=0.52 (95% CI: 0.31-0.86) with log-rank p=0.011. The median PFS was 11.0 months in the combination arm and only 2.8 months in the letrozole+placebo only arm.

Figure 2:
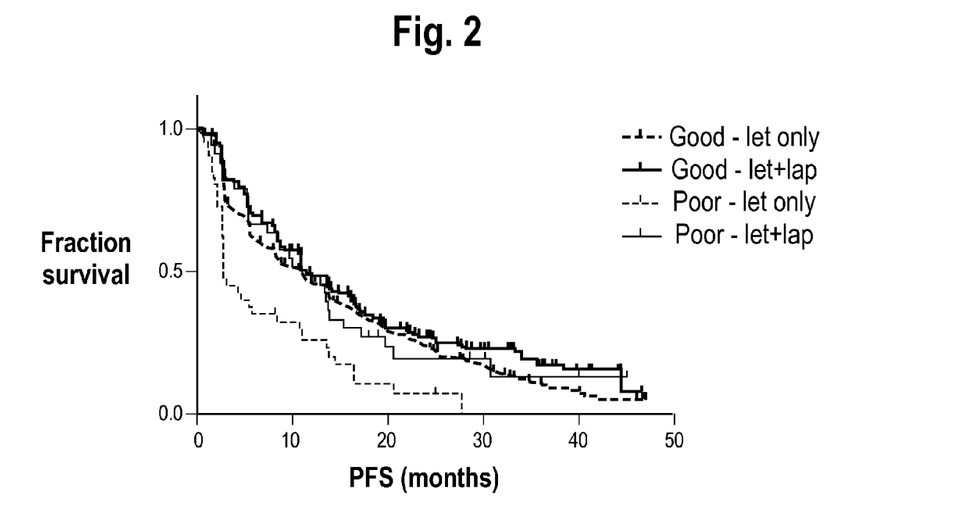
FIG. 2 is a Kaplan-Meier plot of Progression Free Survival (PFS) for overall population by VeriStrat classification and treatment arm.

FIG. 2 is a Kaplan-Meier plot of Progression Free Survival (PFS) for overall population by VeriStrat classification and treatment arm. FIG. 2 shows that patients have similar outcomes on the combination of lapatinib and letrozole regardless of their VeriStrat status, but not on letrozole alone. In particular, FIG. 2 shows that, for those patients treated with letrozole alone, patients identified as "Poor" do much worse on letrozole alone than those patients identified as "Good." FIG. 2 also shows that for patients whose serum was classified as "Poor" showed improved progression free survival (PFS) with the addition of lapatinib to letrozole.

The results of these four comparisons are summarized in Table 2.

TABLE 2

Summary of survival analysis results for PFS for the overall population by treatment arm and VeriStrat classification

| | HR | P value | Median PFS (months) |
|---|---|---|---|
| VS Poor by tx | 0.52 (0.31-0.86) | 0.011 | 2.8 (let); 11.0 (let + lap) |
| VS Good by tx | 0.84 (0.72-0.98) | 0.028 | 10.8 (let); 11.4 (let + lap) |
| Let + lat arm by VS | 0.87 (0.58-1.33) | 0.53 | 11.0 (Poor); 11.4 (Good) |
| Let only arm by VS | 0.36 (0.23-0.58) | <0.0001 | 2.8 (Poor); 10.8 (Good) |

From this data we have discovered that patients whose serum is classified as "Poor" benefit significantly more when treated with lapatinib plus letrozole as compared to treatment with letrozole alone: progression free survival is greater by 8.2 months. The significance of the difference in benefit between the treatment arms was demonstrated in the multivariate analysis that included the interaction term.

Figure 7:
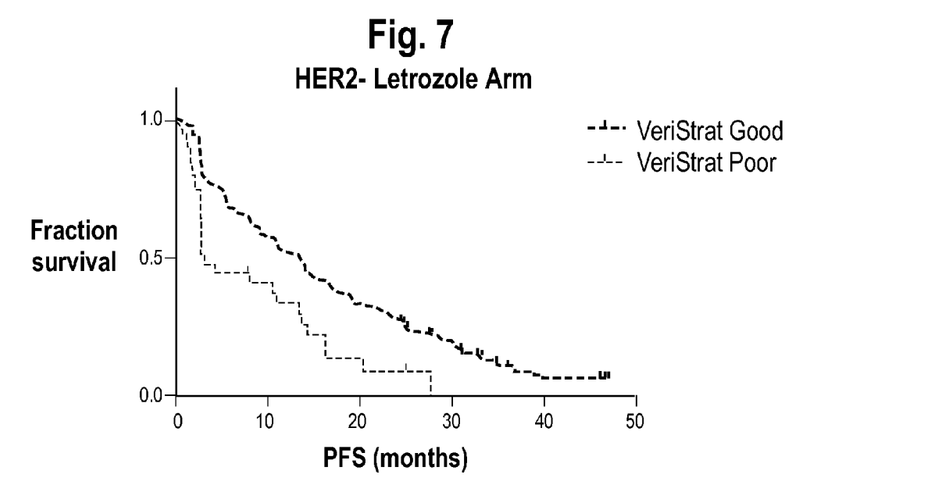
FIG. 7 is a Kaplan-Meier plot of PFS for the letrozole arm by VeriStrat classification for HER2- patients.
Figure 8:
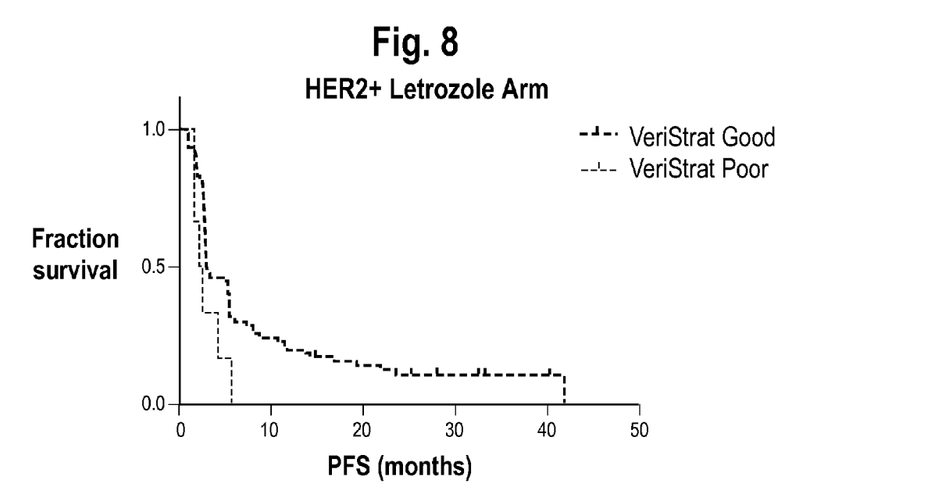
FIG. 8 is a Kaplan-Meier plot of PFS for the letrozole arm by VeriStrat classification for HER2+ patients.

FIGS. 7 and 8 show our data of PFS for patients with known HER2 status receiving letrozole alone. PFS for HER2− patients is shown in FIG. 7 and PFS for HER2+ patients is shown in FIG. 8. With reference to the HER2− data (FIG. 7), in the letrozole+placebo arm, there was significant separation between VeriStrat Good and VeriStrat Poor patients, HR=0.37 (95% CI: 0.21-0.64) and log-rank p=0.0004. The median PFS was 13.6 months for VeriStrat Good patients and 3.1 months for VeriStrat Poor patients. With reference to the HER2+ data (FIG. 8), there was significant separation between VeriStrat Good and VeriStrat Poor patients, HR=0.29 (95% CI: 0.09-0.98) and log-rank p=0.046. The median PFS was 3.0 months for VeriStrat Good patients and 2.3 months for VeriStrat Poor patients.

Considering FIGS. 7 and 8 together, our data demonstrates that our VeriStrat test identifies patients with poor outcomes on letrozole alone independent of HER2 status, i.e., those patients whose serum sample is classified as "Poor" by the classifier.

Figure 9:
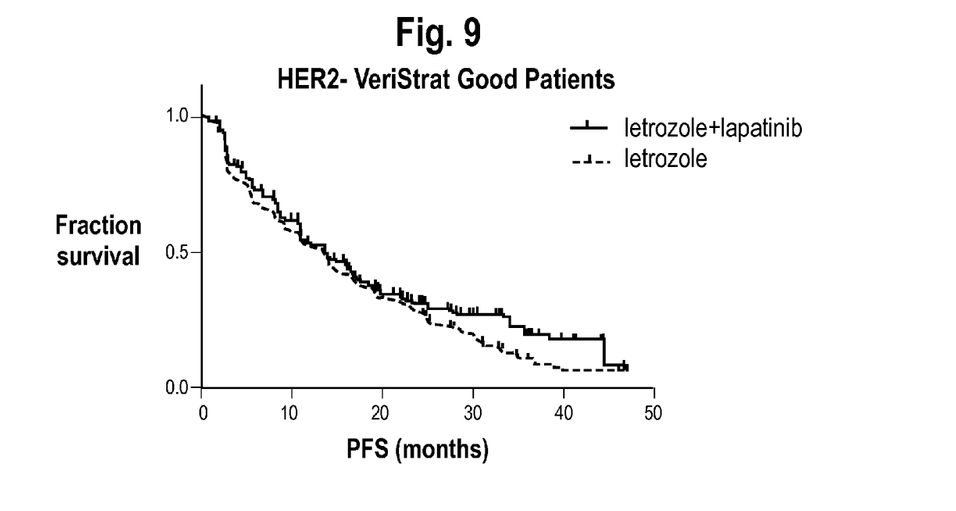
FIG. 9 is a Kaplan-Meier plot of PFS for VeriStrat Good patients by treatment arm for HER2- patients.
Figure 10:
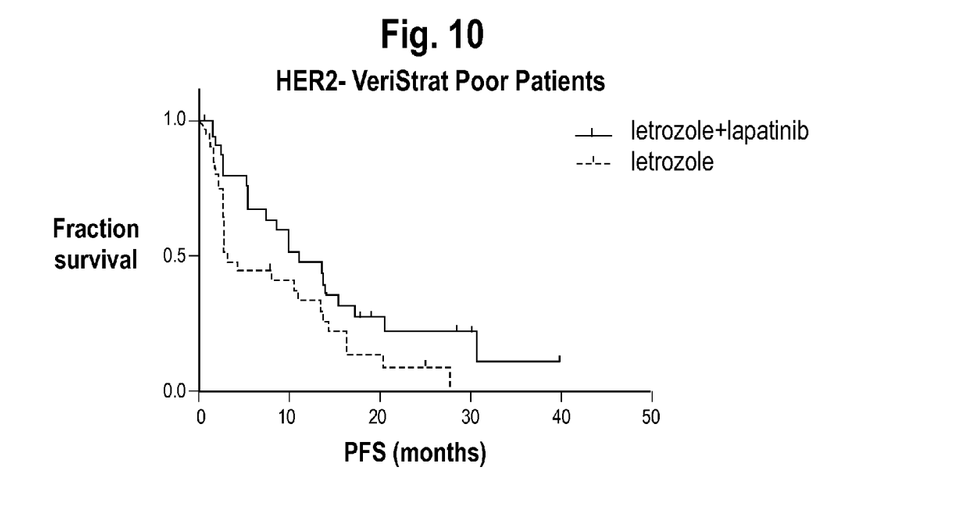
FIG. 10 is a Kaplan-Meier plot of PFS for VeriStrat Poor patients by treatment arm for HER2- patients.

Our data on the effect on PFS with the addition of lapatinib to letrozole in the HER2− population is shown in FIGS. 9 and 10. HER2− VeriStrat "Good" and "Poor" patients were analyzed separately by treatment arm. Data for HER2−, VeriStrat "Good" patients are shown in FIG. 9 and "Poor" patients in FIG. 10. There was no significant separation in either VeriStrat classification group. There may be a trend to separation in favor of letrozole+lapatinib treatment, especially in the VeriStrat "Poor" patients where the number of patients was small. For "Good" patients the HR between treatment arms was 0.85 (95% CI: 0.71-1.02) and log-rank p=0.085. The median PFS was 13.8 months for the combination arm and 13.6 months for the letrozole+placebo arm. For VeriStrat "Poor" patients (FIG. 10), HR=0.57 (95% CI: 0.32-1.04) with log-rank p=0.068. The median PFS was 11.0 months in the combination arm and only 3.1 months in the letrozole+placebo arm.

The results of these four comparisons are summarized in Table 3.

TABLE 3

Summary of survival analysis results for PFS for HER2−
patients by treatment arm and VeriStrat classification

|  | HR | P value | Median PFS (months) |
|---|---|---|---|
| VS Poor by tx | 0.57 (0.32-1.04) | 0.068 | 3.1 (let); 11.0 (let + lap) |
| VS Good by tx | 0.85 (0.71-1.02) | 0.085 | 13.6 (let); 13.8 (let + lap) |
| Let + lat arm by VS | 0.77 (0.46-1.27) | 0.30 | 11.0 (Poor); 13.8 (Good) |
| Let only arm by VS | 0.37 (0.21-0.64) | 0.0004 | 3.1 (Poor); 13.6 (Good) |

FIG. 6 is a Kaplan-Meier plot of Progression Free Survival (PFS) for overall population by VeriStrat classification and treatment arm for the HER2-negative population. FIG. 6 shows that HER2− patients have similar outcomes on the combination of lapatinib and letrozole regardless of their VeriStrat status, but not on letrozole alone. In particular, FIG. 6 shows that, for those patients treated with letrozole alone, patients identified as VeriStrat Poor do much worse on letrozole alone than those patients identified as VeriStrat Good. FIG. 6 also shows that for those HER2− patients whose serum was classified as "Poor" showed a trend for improved progression free survival with the addition of lapatinib to letrozole.

Figure 11:
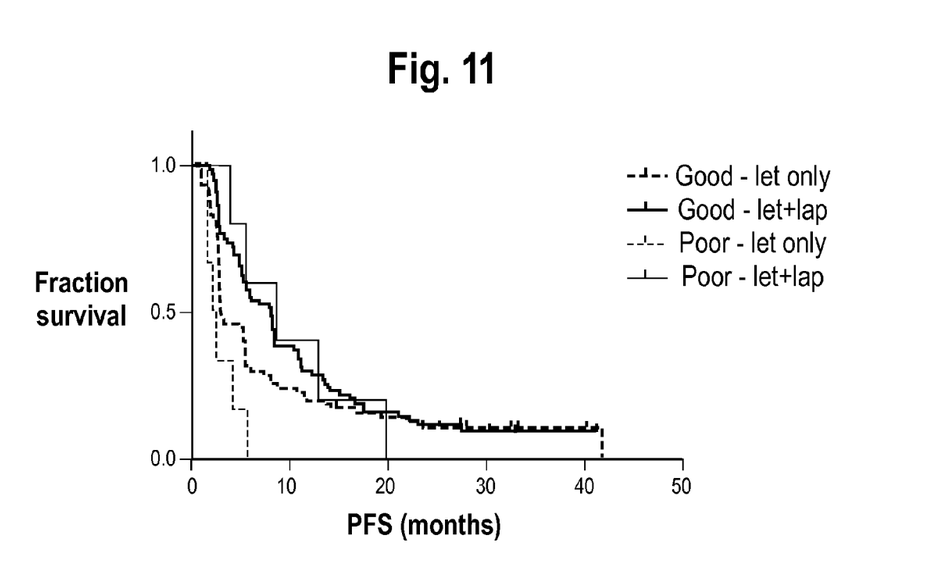
FIG. 11 is a Kaplan-Meier plot of PFS for HER2+ patients by VeriStrat classification and treatment arm. It shows that patients have similar outcomes with lapatinib plus letrozole treatment regardless of their VeriStrat classification.
Figure 12:
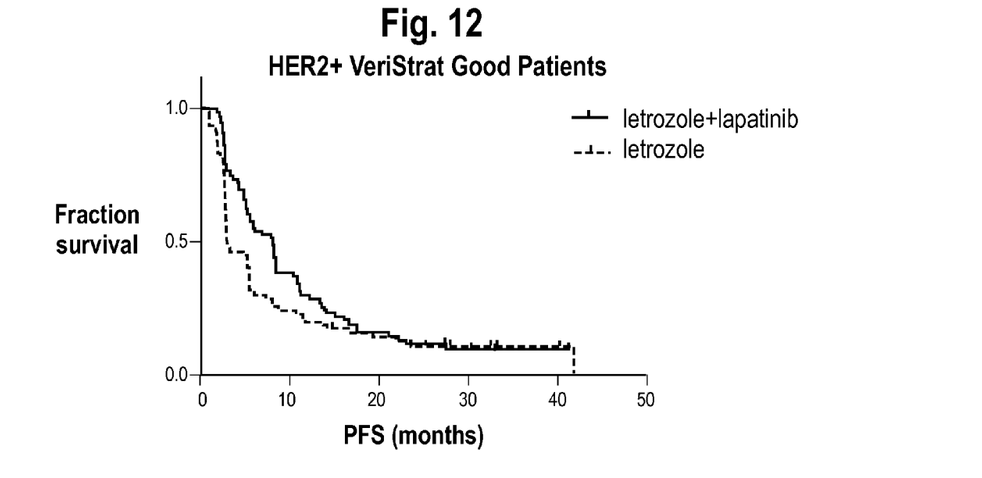
FIG. 12 is a Kaplan-Meier plot of PFS for VeriStrat "Good" patients by treatment arm for HER2+ patients.
Figure 13:
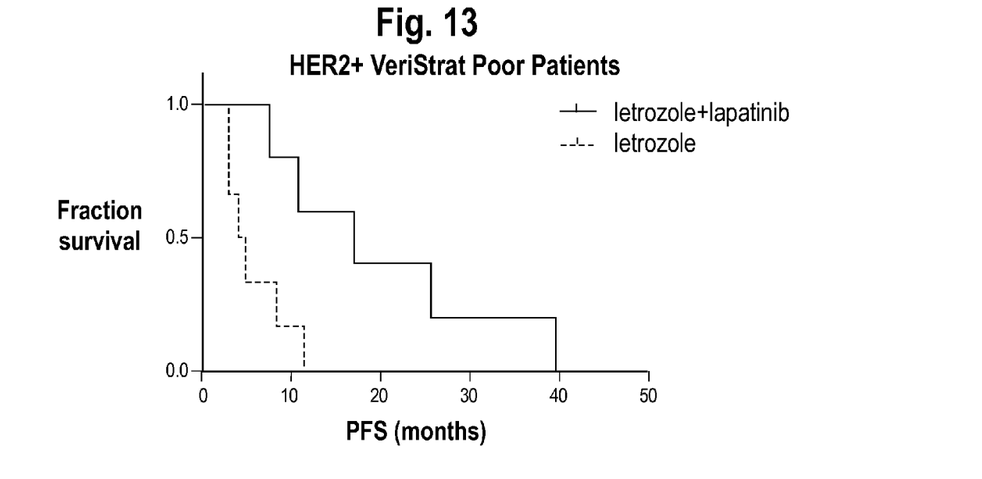
FIG. 13 is a Kaplan-Meier plot of PFS for VeriStrat "Poor" patients by treatment arm for HER2+ patients.

Data showing the effect on PFS with the addition of lapatinib to letrozole in the HER2 positive (HER2+) population is shown in FIGS. 11-13. For HER2+ patients, each treatment arm was analyzed separately by VeriStrat classification. The data for VeriStrat Good patients is shown in FIG. 12. The data for VeriStrat Poor patients is shown in FIG. 13. The combined data for all HER2+ patients and both treatment arms is shown in FIG. 11.

In the HER2+ population, there was significant separation in both VeriStrat classification groups in favor of letrozole+lapatinib treatment. For "Good" patients (FIG. 12) the HR between treatment arms was 0.71 (95% CI: 0.50-0.99) and log-rank p=0.046. The median PFS was 8.0 months for the combination arm and 3.0 months for the letrozole only arm. In "Poor" patients (FIG. 13), the separation is similar with the median PFS of 8.6 months for the combination arm and 2.3 months for the letrozole only arm.

The results of these four comparisons are summarized in Table 4.

TABLE 4

Summary of survival analysis results for PFS for HER2+
patients by treatment arm and VeriStrat (VS) classification

|  | HR | P value | Median PFS (months) |
|---|---|---|---|
| VS Poor by tx | 0.17 (0.04-0.76) | 0.021 | 2.3 (let); 8.6 (let + lap) |
| VS Good by tx | 0.71 (0.50-0.99) | 0.046 | 3.0 (let); 8.0 (let + lap) |
| Let + lat arm by VS | 0.99 (0.40-2.48) | 0.99 | 8.6 (Poor); 8.0 (Good) |
| Let only arm by VS | 0.29 (0.09-0.98) | 0.046 | 2.3 (Poor); 3.0 (Good) |

FIGS. 11, 12 and 13 show that HER2+ patients have similar outcomes with lapatinib plus letrozole treatment regardless of VeriStrat classification.

These results taken together indicate that the VeriStrat Poor patients benefit from the addition of lapatinib to letrozole independently from their HER2 status.

PFS Interaction Analysis

A Cox Proportional Hazard Model analysis was carried out including VeriStrat classification, treatment arm, and an interaction term between the two. The results are shown in Table 5. Treatment and VeriStrat classification were both significant, as was the interaction term, indicating that the difference in Hazard Ratio (HR) between VeriStrat Good and VeriStrat Poor patients is significantly different between the letrozole+placebo arm and the letrozole+lapatinib arm.

TABLE 5

Results of the Cox Proportional Hazards
Model with Covariate Selection

|  | HR | 95% CI | P value |
|---|---|---|---|
| VeriStrat Classification (good vs poor) | 0.41 | 0.29-0.58 | <0.0001 |
| Treatment Arm (Let + Lap vs Let) | 0.36 | 0.22-0.60 | <0.0001 |
| HER2 Status HER2+ vs HER2− | 1.76 | 1.46-2.13 | <0.0001 |
| ECOG PS (>1 vs 0) | 1.43 | 1.23-1.66 | <0.0001 |
| Prior adjuvant hormonal therapy (<6 months vs >6 months) | 0.54 | 0.45-0.65 | <0.0001 |
| Hormone receptor status (ER− and PgR− vs ER+ and/or PgR+) | 1.48 | 1.01-2.18 | 0.046 |
| No. of metastatic sites (≥3 vs <3) | 1.56 | 1.34-1.81 | <0.0001 |
| Veristrat*treatment interaction | 2.31 | 1.36-3.94 | 0.0020 |

While the EGF30008 study involved a single targeted therapy (lapatinib) and a single aromatase inhibitor (letrozole), there are several dual HER2 and EGFR inhibitors under investigations, e.g. neratinib, afatinib, ARRY-543 that are likely examples of other targeted therapies that could be used in the method. Also, the effect of the combination of EGFR inhibitors (erlotinib, gefitinib) and HER2 inhibitor (trastuzumab) may be similar to one of the dual inhibitors.

Letrozole belongs to the class of selective reversible aromatase inhibitors, as well as Anastrozole (Arimidex); another similar acting, however non-reversible, agent is Exemestane (Aromasin). The methods of this disclosure may be used to predict HER2−, post-menopausal hormone receptor positive breast cancer patient benefit from the combination of targeted therapies and an aromatase inhibitor other than letrozole.

DEFINITIONS

As used herein, the terms "endocrine therapy" and "endocrine therapy drugs" should be interpreted to mean those drugs which influence the endocrine system by modulating estrogen synthesis and/or estrogen receptor pathways, including but not limited to SERDs, SERMs and aromatase inhibitors.

The term "targeted therapies" should be interpreted to mean those drugs targeting specific pathways within the cell, including but not limited to EGFR-Is, HER2 inhibitors, lapatinib and combinations thereof.

The term "hormone receptor positive" is intended to include estrogen (ER) and/or progesterone (PgR) receptors-positive breast cancer patients.

All questions concerning the scope of the invention are to be answered by reference to the appended claims.

REFERENCES

1. Goldhirsch, A., M. Colleoni, and R. D. Gelber, *Endocrine therapy of breast cancer*. Ann Oncol, 2002. 13 Suppl 4: p. 61-8.

2. Ma, C. X., C. G. Sanchez, and M. J. Ellis, *Predicting endocrine therapy responsiveness in breast cancer.* Oncology (Williston Park), 2009. 23(2): p. 133-42.
3. Johnston, S., et al., *Lapatinib combined with letrozole versus letrozole and placebo as first-line therapy for postmenopausal hormone receptor-positive metastatic breast cancer.* J Clin Oncol, 2009. 27(33): p. 5538-46.
4. Chlebowski, R. T., *Optimizing aromatase inhibitor integration into initial treatment strategies in postmenopausal women with hormone-receptor-positive early breast cancer.* Breast Cancer Res Treat, 2008. 112 Suppl 1: p. 25-34.
5. Seruga, B. and I. F. Tannock, *Up-front use of aromatase inhibitors as adjuvant therapy for breast cancer: the emperor has no clothes.* J Clin Oncol, 2009. 27(6): p. 840-2.
6. Dowsett, M., et al., *Meta-analysis of breast cancer outcomes in adjuvant trials of aromatase inhibitors versus tamoxifen.* J Clin Oncol, 2010. 28(3): p. 509-18.
7. Cuzick, J., *The ATAC trial: the vanguard trial for use of aromatase inhibitors in early breast cancer.* Expert Rev Anticancer Ther, 2007. 7(8): p. 1089-94.
8. Tobias, J. S. and A. Howell, *An open randomised trial of second-line endocrine therapy in advanced breast cancer: comparison of the Aromatase inhibitors letrozole and anastrozole.* Eur J Cancer, 2004. 40(12): p. 1913.

We claim:

1. A method of determining whether a post-menopausal hormone receptor positive breast cancer patient with HER2-negative status is likely to benefit from administration of a combination treatment comprising administration of a targeted anti-cancer drug in addition to an endocrine therapy drug, comprising the steps of:
    a) conducting mass spectrometry on a blood-based sample from the patient with a mass-spectrometer and thereby obtaining a mass spectrum of the blood-based sample;
    b) performing one or more predefined pre-processing steps on the mass spectrum obtained in step a);
    c) obtaining, using a programmed computer, integrated intensity values of selected features in said mass spectrum at one or more predefined m/z ranges after the pre-processing steps on the mass spectrum in step b) have been performed, wherein the one or more predefined m/z ranges is selected from the group of m/z ranges consisting of:
    5732 to 5795
    5811 to 5875
    6398 to 6469
    11376 to 11515
    11459 to 11599
    11614 to 11756
    11687 to 11831
    11830 to 11976
    12375 to 12529
    23183 to 23525
    23279 to 23622 and
    65902 to 67502;
    d) executing, in said programmed computer, a classification algorithm comparing the integrated intensity values obtained in step c) to features in the stored set of mass spectral data and obtaining a class label for the sample, wherein the programmed computer comprises a stored set of class-labeled mass spectral data from blood-based samples from other treated solid epithelial tumor cancer patients; and
    e) identifying the patient as being likely to benefit from the combination treatment if the class label for the sample obtained by the classification algorithm in step d) is "Poor" or the equivalent.

2. The method of claim 1, wherein the targeted anti-cancer drug comprises lapatinib.

3. The method of claim 1, wherein the endocrine therapy drug comprises an aromatase inhibitor.

4. The method of claim 3, wherein the aromatase inhibitor comprises letrozole.

5. The method of claim 1, wherein the endocrine therapy drug comprises a selective estrogen receptor modulator (SERM).

6. The method of claim 5, wherein the endocrine therapy drug comprises selective estrogen receptor downregulator (SERD).

7. The method of claim 5, wherein the endocrine therapy drug comprises tamoxifen or the equivalent.

8. The method of claim 1, wherein the stored set of class-labeled mass spectral data from blood-based samples from other treated solid epithelial tumor cancer patients used in the classification step d) comprise class-labeled spectra of samples obtained from non-small cell lung cancer patients and the class labels indicate whether such patients benefitted from treatment with an epidermal growth factor receptor inhibitor ("Good") or did not benefit ("Poor").

* * * * *